United States Patent [19]

Jaksch

[11] Patent Number: 5,959,112
[45] Date of Patent: Sep. 28, 1999

[54] PROCESS FOR THE PREPARATION OF ROPIVACAINE HYDROCHLORIDE MONOHYDRATE

[75] Inventor: Peter Jaksch, Järna, Sweden

[73] Assignee: Astra Aktiebolag, Sodertalje, Sweden

[21] Appl. No.: 08/647,994

[22] PCT Filed: Apr. 30, 1996

[86] PCT No.: PCT/SE96/00563

§ 371 Date: Nov. 21, 1996

§ 102(e) Date: Nov. 21, 1996

[87] PCT Pub. No.: WO96/36606

PCT Pub. Date: Nov. 21, 1996

[30] Foreign Application Priority Data

May 16, 1995 [SE] Sweden ................................ 9501808

[51] Int. Cl.$^6$ .................................................. C07D 211/30
[52] U.S. Cl. .............................................................. 546/225
[58] Field of Search ............................................... 546/225

[56] References Cited

FOREIGN PATENT DOCUMENTS 0151110  3/1989  European Pat. Off. .
0239710  9/1990  European Pat. Off. .
1180712  2/1970  United Kingdom .

OTHER PUBLICATIONS

Acta Chemica Scandinavica B 41 (1987), pp. 757–761, Federsel, et al., An Efficient Synthesis of a New, Chiral 2',6'–Pipe–cologylidide.

Journal of Medicinal Chemistry, vol. 14, No. 9, (1971), pp. 891–892.

*Primary Examiner*—John Kight
*Assistant Examiner*—Raymond Covington
*Attorney, Agent, or Firm*—White & Case L.L.P.

[57] ABSTRACT

New process for the preparation of ropivacaine hydrochloride monohydrate adapted for production in the plant, which process includes three steps.

20 Claims, No Drawings

PROCESS FOR THE PREPARATION OF ROPIVACAINE HYDROCHLORIDE MONOHYDRATE

FIELD OF THE INVENTION

The present invention relates to a new process for the preparation of ropivacaine hydrochloride monohydrate.

BACKGROUND AND PRIOR ART

The problem underlying the present invention was to provide a new process adapted for production in the plant, giving a reproducible high enantiomeric yield and a high optical purity.

Ropivacaine hydrochloride monohydrate is the generic name for the compound (S)-(−)-1-propyl-2',6'-pipecoloxylidide hydrochloride monohydrate, which compound is a local anesthetic described in EP 0 239 710. It is prepared by adding water and hot acetone to ropivacaine hydrochloride whereafter the desired product is crystallized. The process for the preparation of the starting material ropivacaine hydrochloride, is described in EP 0 151 110.

GB patent no. 1,180,712 discloses a process for the preparation of levo-1-n-butyl-2',6'-pipecoloxylidide. Said process includes a first step of resolving dl-2',6'-pipecoloxylidide, whereby dl-2',6'-pipecoloxylidide is reacted with 0,0-dibenzoyl-d-tartaric acid and thereafter the resulting mixture of diastereoisomeric 0,0-dibenzoyl-d-tartrates is reacted with boiling acetone, the acetone-insoluble dextro-2',6'-pipecoloxylidide salt is separated and the levo-2',6'-pipecoloxylidide salt is isolated from the acetone solution. However, the described process is intricate and includes isolating the product from hot acetone, i.e. it is a plain method for laboratories which could not be used for production in the plant.

The idea of using a resolution method to obtain the longer acting single enantiomers of the local anesthetics mepivacaine and bupivacaine was published in J Med Chem 14:891–892, 1971. A mixture of 2',6'-pipecoloxylidide was treated with dibenzoyl-L-tartaric acid monohydrate whereby isopropanol was added separating the isopropanol-insoluble enantiomer whereafter the desired enantiomer was isolated. Using isopropanol does not give a crystallisation system which is stable during the time required for production in the plant. This is because the solution is supersaturated with the undesired enantiomer, and thus a crystallization of the wrong shape could easily be started by small disturbances which means that isopropanol is not suitable to use for production in large scale.

In Acta Chem Scand B41: 757–761, 1987 it is described to use isopropanol in combination with various water-contents for the resolution step. These combinations gave varying yield and quality. Also the combination of isopropanol and water gave a crystallisation system not enough stable for production in the plant.

OUTLINE OF THE INVENTION

The present invention is directed to a process suitable for the large scale preparation of ropivacaine hydrochloride monohydrate, which is a compound of the formula (I)

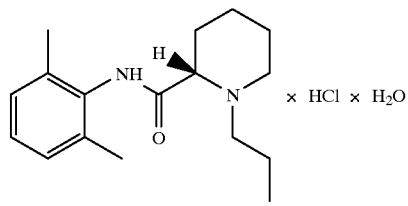

This new process comprises three steps, the first step being a resolution step.

It has been found that by using a resolving agent forming a stable crystallization system with water, preferably a combination of a ketone and water, it is possible to separate the undesired (R)-pipecoloxylidide and isolate the (S)-pipecoloxylidide in this first step. Thus, a crystallisation system which is stable for up to 24 hours is achieved, which is sufficient for production in the plant.

It is not possible to increase the enantiomeric yield in any of the two subsequent steps, which means that this first step is of major importance. Thus, a further aspect of the present invention was to obtain a reproducable high enantiomeric yield and a high optical purity in the first step. This was achieved by using the combination of a ketone, which together with water forms a stable crystallization system, and water.

The new process according to the present invention for the preparation of the compound (I) comprises the following steps:

Step 1 (i) The racemic starting material pipecoloxylidide hydrochloride of the formula (II)

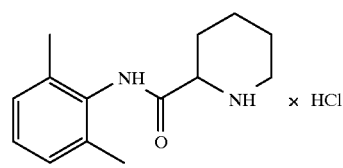

is liberated from its HCl salt, by extraction to an organic solvent with diluted base;

(ii) pipecoloxylidide is resolved by crystallization with a resolving agent forming a stable crystallization system with water, and the crystalline product is liberated from its salt by extraction in an organic solvent which dissolves a minimum of about 1% (w/w) of water with diluted base, giving the compound (S)-pipecoloxylidide of the formula (III)

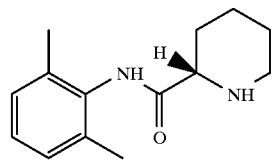

Step 2) (i) S-pipecoloxylidide of the formula (III) is alkylated with a 1-halopropane, preferably 1-bromopropane or 1-iodopropane, in the presence of a base and optionally in the presence of a catalyst, the reaction is completed by heating, preferably to reflux temperature, or optionally at a lower temperature which however means that the reaction is completed more slowly, whereafter the inorganic salts are removed by extraction with water;

(ii) The solution achieved in step 2 (i) is optionally diluted and the product is precipitated as ropivacaine hydrochloride of the formula (IV)

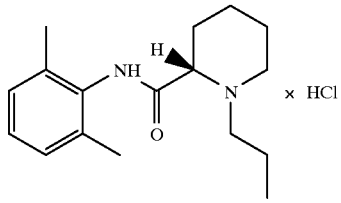

which thereafter is isolated;

Step 3: The product (IV) achieved in step 2 (ii), is dissolved in aqueous acetone, preferably at reflux temperature, the product (I) is precipitetted by addition of acetone, and the product is finally isolated and dried.

Resolving agents that may be used in step I (i) are L-(−)-dibenzoyl tartaric acid or L-(−)-ditoluoyl tartaric acid, L-(−)-dibenzoyl tartaric acid being the preferred resolving agent.

The diluted base in step 1 (i) is preferably selected from sodium hydroxide, potassium hydroxide, sodium carbonate or potassium carbonate.

Preferred resolving agents for the crystallization in step 1 (ii) are ketones forming a stable crystallization system together with water. Preferred solvents for this crystallization are acetone or ethyl methyl ketone, the most preferred being acetone.

Preferably the water content of the organic solvent used in the crystallization step 1 (ii) is 15–25%, most preferably 20%.

The organic solvent used in the extraction step 1 (ii) should dissolve a minimum of about 1% (w/w) of water. If not, the reaction is performed in a two-phase system. Furthermore, an additional amount of water, about 5%, should preferably be present during the reaction.

The choice of the organic solvent used for the extraction of step 1 (ii) will be appreciated by a skilled person. However, the organic solvent is preferably selected from isobutyl methylketone, acetonitrile, ethanol, butanol or toluene, but other solvents may also be used. Isobutyl methylketone is particularly preferred.

The alkylation reaction of step 2(i) is performed in the presence of a base and preferably in the presence of a catalyst. If 1-iodopropane is used as the alkylating reagent, the use of a catalyst is not necessary in order for the reaction to be performed. However, the reaction could be very time-consuming if no catalyst is used.

Bases that can be used in the reaction step 2 (i) will be appreciated by a person skilled in the art. However, carbonates, in particular potassium carbonate or sodium carbonate, or amines, in particular triethylamine, are preferred. Most preferably potassium carbonate is the base of choice.

The catalyst used in step 2 (i) is an iodide catalyst, preferably sodium iodide.

The solution achieved in step 2 (i) is preferably diluted with acetone in step 2(ii).

DETAILED DESCRIPTION OF THE INVENTION

The invention will now be described in more detail by the following examples.

EXAMPLE 1

Step 1, resolution

Pipecoloxylidide hydrochloride (1.0 kg), acetone (3.75 L), and water (0.85 L) were charged. NaOH(aq) was added to pH>11. The phases, thus formed, were separated and the organic phase was diluted with water (1.4 L). L-(−)-dibenzoyltartaric acid (0.67 kg), dissolved in acetone (3.75 L), was added. The solution was seeded. The crystal slurry was cooled to 2° C. The crystals were collected by centrifugation and were washed with acetone followed by isobutyl methyl ketone. The product was not dried. The moist crystalline product was extracted with isobutyl methyl ketone (3.60 L) and diluted NaOH (2.60 L) at pH>11. The phases were separated. The organic phase was washed with water (0.6 L) and was used directly in the next step. Yield (calc. on the dry basis): ~0.39 kg of (S)-pipecoloxylidide (~90%).

EXAMPLE 2

Step 2, alkylation and salt precipitation

Example 2A:

$K_2CO_3$ (0.32 kg), NaI (catalytical amount), and 1-bromopropane (0.28 kg) and about 5% of water, were added to the organic phase from the previous step. The mixture was heated to reflux to complete the reaction. The excess of bromopropane was removed by distillation. The reaction mixture was extracted with water (1.70 L). Acetone (1.70 L) was added to the organic phase followed by HCl(aq) to pH ~2. The solution was seeded. The crystal slurry was cooled to 9° C. The crystals were collected by centrifugation and were washed with acetone. The product was used directly in the next step and was not dried. Yield (calc. on the dry basis): 0.47 kg of ropivacaine hydrochloride (~0.90%).

Example 2B:

As an alternative, the following procedure was followed. $K_2CO_3$ (0.32 kg), NaI (catalytical amount), 1-bromopropane (0.28 kg) and water (1.70 L) were added to the organic phase from the previous step. The mixture was heated to reflux to complete the reaction. The excess of bromopropane was removed by distillation. The reaction mixture was separated. Acetone (1.70 L) was added to the organic phase followed by HCl(aq) to pH ~2. The solution was seeded. The crystal slurry was cooled to 9° C. The crystals were collected by centrifugation and were washed with acetone. The product was used directly in the next step and was not dried. Yield (calc. on the dry basis): 0.47 kg of ropivacaine hydrochloride (~0.90%).

EXAMPLE 3

Step 3, recrystallisation

Ropivacaine hydrochloride, from the previous step, was slurried in acetone (1.0 L) at reflux temperature. Water (0.60 L) was added. The resulting mixture was filtered and acetone (7.6 L) was added at >40° C. The solution was seeded. The slurry of crystals was cooled to 3° C. The crystals were collected by centrifugation and were washed with acetone. The crystals were dried at 30–40° C. in vacuum (<20 kPa). Yield: ~0.42 kg of ropivacaine hydrochloride monohydrate (~80%).

The chemical analysis of the end product was performed by NMR analysis as indicated below.

The NMR spectra were obtained from a solution of 22 mg in 0.7 ml deuterium oxide (99.95) % at 23° C. t-Butanol was used as internal reference (i.r). The instrument used was a Varian Gemini 300.

The numbers in the assignment list is reffering to the structure and numbering as given in the formula below. The results are given both in a proton spectrum (Table 1) and in a $C^{13}$-spectrum (Table 2).

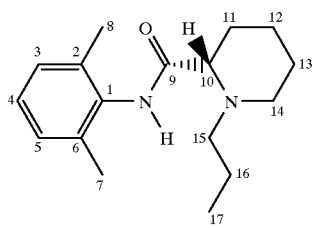

TABLE 1

Proton spectrum operating at 300.1 MHz. $\delta_{(i.r.)} = 1.23$ ppm

| Shift (ppm) | Integral | Multiplicity | Assignment |
|---|---|---|---|
| 0.96 | 3H | triplet | 17 |
| 1.69–2.0 | 7H | multiplets | 11a, 12, 13, 16 |
| 2.18 | 6H | singlet | 7, 8 |
| 2.41–2.45 | 1H | broad doublet | 11e |
| 3.09–3.18 | 3H | multiplet | 15, 14a |
| 3.70–3.74 | 1H | broad doublet | 14e |
| 4.15–4.19 | 1H | double doublet | 10 |
| 4.78 | 3H | singlet | $H_2O$, $N^+$—H |
| 7.18–7.28 | 3H | multiplet | 3, 4, 5 |

TABLE 2

$C^{13}$ spectrum operating at 75.5 MHz. $\delta_{(i.r.)} = 30.6$ ppm

| Carbon No. | Shift |
|---|---|
| 17 | 11.20 |
| 16 | 17.88 |
| 7, 8 | 18.22 |
| 12[1] | 21.86 |
| 13[1] | 23.30 |
| 11 | 29.93 |
| 14 | 53.11 |
| 15 | 58.86 |
| 10 | 66.76 |
| 3, 5 | 129.31 |
| 4 | 129.56 |
| 1 | 132.87 |
| 2, 6 | 136.72 |
| 9 | 169.40 |

[1]Assignment may be interchanged.

I claim:

1. A process for the preparation of ropivacaine hydrochloride monohydrate of the formula (I)

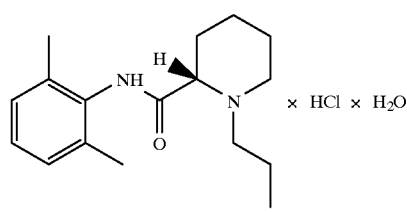

comprising the following reaction steps:

Step 1
(i) The racemic starting material pipecoloxylidide hydrochloride of the formula (II)

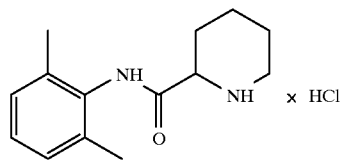

is liberated from its HCl salt, by extraction to an organic solvent with diluted base;

(ii) pipecoloxylidide is resolved by crystallization with a resolving agent forming a stable crystallization system with water, and the crystalline product is liberated from its salt by extraction in an organic solvent which dissolves a minimum of about 1% (w/w) of water with diluted base, giving the compound (S)-pipecoloxylidide of the formula (III)

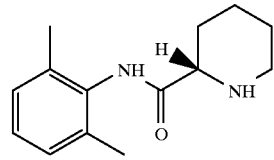

Step 2)
(i) S-pipecoloxylidide of the formula (III) is alkylated with a 1-halopropane, in the presence of a base and optionally in the presence of a catalyst, the reaction is completed by heating, whereafter the inorganic salts are removed by extraction with water;

(ii) The solution achieved in step 2 (i) is optionally diluted and the product is precipitated as ropivacaine hydrochloride of the formula (IV)

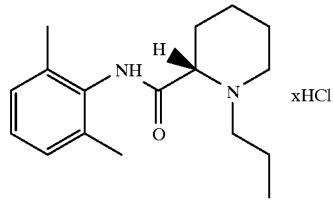

which thereafter is isolated;

Step 3: The product (IV) achieved in step 2 (ii), is dissolved in aqueous acetone, the product (I) is precipiteted by addition of acetone, and the product is finally isolated and dried.

2. A process according to claim 1, whereby the resolving agent forming a stable crystallization system together with water in step 1(ii) is a ketone.

3. A process according to claim 2, whereby the ketone is selected from acetone and ethyl methyl ketone.

4. A process according to claim 3, whereby the ketone is acetone.

5. A process according to claim 1, whereby the water content of the organic solvent used in the crystallization step 1(ii) is 15–25%.

6. A process according to claim 5, whereby the water content is 20%.

7. A process according to claim 1, whereby the diluted base in step 1 (i) is selected from sodium hydroxide, potassium hydroxide, sodium carbonate or potassium carbonate.

8. A process according to claim 1, whereby the resolving agent in step 1(i) is L-(–)-dibenzoyl tartaric acid or L-(–)-ditoluoyl tartaric acid.

9. A process according to claim 8, whereby the resolving agent is L-(–)-dibenzoyl tartaric acid.

10. A process according to claim 1, whereby the organic solvent used for the extraction of step 1(ii) is selected from isobutyl methylketone, acetonitrile, ethanol, butanol or toluene.

11. A process according to claim 10, whereby the organic solvent used for the exctraction is isobuthyl methylketone.

12. A process according to claim 1, whereby the alkylation of step 2(i) is performed in the presence of a catalyst and at reflux temperature.

13. A process according to claim 1, whereby the alkylation reagent of step 2(i) is 1-bromopropane or 1-iodopropane.

14. A process according to claim 1, whereby the base in step 2(i) is a carbonate or an amine.

15. A process according to claim 14, whereby the base in step 2(i) is selected from potassium carbonate, sodium carbonate and triethylamine.

16. A process according to claim 15, whereby the base in step 2(i) is potassium carbonate.

17. A process according to claim 1, whereby the catalyst in step 2(i) is an iodide catalyst.

18. A process according to claim 17, whereby the catalyst is sodium iodide.

19. A process according to claim 1, whereby the reaction of step 1(ii) is performed in a two-phase system.

20. A process according to claim 1, whereby an additional amount of water of approximately 5% is present during the reaction of step 1(ii).

* * * * *

UNITED STATES PATENT AND TRADEMARK OFFICE
CERTIFICATE OF CORRECTION

PATENT NO. : 5,959,112
DATED : September 28, 1999
INVENTOR(S) : Peter Jaksch

It is certified that error appears in the above-identified patent and that said Letters Patent is hereby corrected as shown below:

Col. 6, line 57, delete "and" and substitute --or-- therefor.

Col. 7, line 11, delete "isobuthyl" and substitute --isobutyl-- therefor.

Col. 8, line 5, delete "and" and substitute --or-- therefor.

Signed and Sealed this

Twentieth Day of June, 2000

*Attest:*

Q. TODD DICKINSON

*Attesting Officer*     *Director of Patents and Trademarks*